United States Patent [19]

Jensen et al.

[11] Patent Number: 5,604,129
[45] Date of Patent: Feb. 18, 1997

[54] THERMOPHILIC FUNGAL EXPRESSION SYSTEM

[75] Inventors: Ejner B. Jensen; Karuppan C. Boominathan, both of Davis, Calif.

[73] Assignee: Novo Nordisk Biotech, Inc., Davis, Calif.

[21] Appl. No.: 457,201

[22] Filed: Jun. 1, 1995

Related U.S. Application Data

[62] Division of Ser. No. 278,473, Jul. 20, 1994.

[51] Int. Cl.⁶ .................................................. C12N 1/15
[52] U.S. Cl. ........................... 435/254.11; 435/911
[58] Field of Search ........................ 435/254.1, 254.11, 435/254.3, 122.3, 320.1, 69.1, 911

[56] References Cited

U.S. PATENT DOCUMENTS

| | | | |
|---|---|---|---|
| 4,732,910 | 3/1988 | Yaginuma et al. | 514/475 |
| 5,089,530 | 2/1992 | Tsipouras et al. | 514/682 |
| 5,364,770 | 11/1994 | Berka et al. | 435/69.1 |

FOREIGN PATENT DOCUMENTS

| | | |
|---|---|---|
| 0566897A2 | 3/1993 | European Pat. Off. . |
| 0610842A2 | 2/1994 | Germany . |
| 0618298A2 | 3/1994 | Germany . |

OTHER PUBLICATIONS

Jain et al., MGG, vol. 234, No. 3, pp. 489–493, 1992.
Allison et al., Current Genetics, vol. 21, No. 3, pp. 225–229, 1992.
Christensen et al., Biotechnology, vol. 6, pp. 1419–1422, 1988.
Drocourt et al., Nucleic Acids Research, vol. 18, No. 13, 1990.
Onions et al., *Smith's Introduction to Industrial Mycology*, 7th ed., 1981, John Wiley & Sons, New York, pp. 142–144.

*Primary Examiner*—James S. Ketter
*Attorney, Agent, or Firm*—Steve T. Zelson, Esq.; Cheryl H. Agris, Esq.

[57] ABSTRACT

The present invention relates to recombinant thermophilic host cells comprising a nucleic acid sequence encoding a heterologous protein, and a method of producing recombinant protein utilizing same. The recombinant hosts of the present invention provide a better morphology in tank fermentations than many known fungal host cells, such as Aspergillus, which morphology results in lower viscosity levels, and therefore improved productivity.

5 Claims, 3 Drawing Sheets

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 57 base pairs
        ( B ) TYPE: nucleic acid
        ( C ) STRANDEDNESS: single ( D ) TOPOLOGY: linear ( x i ) SEQUENCE DESCRIPTION: SEQ ID NO:1:

GCTCAGAAGC TTCCATCCTA CACCTCAGCA ATGTCGCCTG AACTCACCGC GACGTCT    57

( 2 ) INFORMATION FOR SEQ ID NO:2:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2:

TCGTACTCTA GAGACCTCGA TAAGGAAACG GGAGCCTGC    39

THERMOPHILIC FUNGAL EXPRESSION SYSTEM

This is a divisional application of co-pending application Ser. No. 08/278,473, filed Jul. 20, 1994 the contents of which are incorporated herein by reference in their entirety.

FIELD OF THE INVENTION

The present invention relates to host cells useful in the production of recombinant proteins. In particular, the invention relates to thermophilic fungal host cells which can be used in the expression of recombinant proteins, especially enzymes.

BACKGROUND OF THE INVENTION

The use of recombinant host cells in the expression of heterologous proteins has in recent years greatly simplified the production of large quantities of commercially valuable proteins, which otherwise are obtainable only by purification from their native sources. Currently, there is a varied selection of expression systems from which to choose for the production of any given protein, including prokaryotic and eukaryotic hosts. The selection of an appropriate expression system will often depend not only on the ability of the host cell to produce adequate yields of the protein in an active state, but also to a large extent may be governed by the intended end use of the protein.

Although mammalian and yeast cells have been the most commonly used eukaryotic hosts, filamentous fungi have now begun to be recognized as very useful as host cells for recombinant protein production. Certain species of the genus Aspergillus have been used effectively as host cells for recombinant protein production. Furthermore, there are often problems with the formation of too dense aggregates of mycelium and uneven distribution, which also results in starvation for nutrients and an unproductive situation. The species Aspergillus nidulans has been reported to be transformed with recombinant plasmids (Ballance, et al. Biochem. Biophys. Res. Comm. 112:284–289, 1983), but transformation was found to occur at fairly low frequency. Both Aspergillus niger and Aspergillus oryzae have also been described as being useful in recombinant production of heterologous proteins. Although these species are currently routinely used in recombinant protein production, they are not without their drawbacks. In particular, their growth morphology in fermentors are not optimum for fermentation, as viscosity tends to become rather high as biomass increases. Increased viscosity limits the ability to mix and aerate the fermentation culture, leading to oxygen and nutrient starvation of the mycelia, which therefore become inviable and unproductive. Furthermore, there are often problems with the formation of too dense aggregates of mycelium, and uneven distribution, which also results in starvation for nutrients. Therefore, for commercial purposes, there continues to be a need for fungal hosts which are capable of use in expression of recombinant proteins but which exhibit satisfactory growth characteristics, such as rapid growth and low viscosity, thereby enhancing productivity in fermentors.

SUMMARY OF THE INVENTION

The present invention provides novel recombinant fungal host cells, which cells exhibit growth characteristics particularly well suited for use in production of heterologous proteins in fermentors. The host cells of the invention are capable of rapid growth, exhibit low viscosity at a given biomass concentration and result in an evenly dispersed mycelium with a loose enough structure to allow sufficient diffusion of nutrients to all parts of the mycelium. In particular, the host cells of the invention are thermophilic fungi, which under equivalent fermentation conditions, for example, in batch fermentation at pH 5, in a salt, yeast extract medium containing 100 g/l glucose, produce viscosity values, measured, for example, in pascal, which are less than 80%, preferably less than 50%, and most preferably less than 30% the viscosity values produced under the same conditions at the same biomass by Aspergillus oryzae; the preferred fungal hosts produce a homogeneous, loose structure of the mycelium. Most preferably, the fungal host cells are selected from the group consisting of Thielavia sp., Thermoascus sp., Myceliophthora sp., and Sporotrichum sp. The invention therefore provides recombinant host cells, as defined above, comprising a nucleic acid fragment encoding a heterologous protein(which is herein understood also to encompass peptides), which protein can be expressed by the host cell. The invention further provides a method for production of heterologous proteins comprising culturing a host cell of the invention under conditions conducive to the expression of the heterologous protein of interest, and recovering the protein from culture.

DETAILED DESCRIPTION OF THE INVENTION

The commercial use of any recombinant protein largely depends on the ability to achieve efficient production in large-scale fermentation. Productivity is limited by a number of factors in industrial fermentations of fungi. The common problems are related to relatively high viscosity compared to unicellular organisms, such as Saccharomyces cerevisiae and Bacillus sp., and the often very heterogeneous distribution of mycelium in dense aggregates, that cause a major part of the mycelium to starve, due to lack of $O_2$ and/or nutrient diffusion to all cells. The high viscosity reduces the oxygen transfer rate that can be reached in the fermentor, which in turn adversely effects the overall energy the cells can produce, thereby leading to lower concentration of obtainable productive biomass and lower final product yield or longer fermentation times. It can therefore be seen that simply increasing biomass is not, without the proper morphology that leads to low viscosity, adequate to increase yield in fermentation. There must be an increase in productive biomass in order for any advantages to be obtained.

It has now been discovered that a number of thermophilic fungi unexpectedly exhibit certain growth characteristics which render them suitable for culturing in fermentors. Attempts to identify fungi with useful growth characteristics begins as a random screening of a taxonomically heterogeneous group of thermophilic fungi under a variety of culture conditions. Shake flask evaluations focus in large part on determining whether the candidate strains produce large quantities of extracellular proteins and/or proteases, each of which is an undesirable characteristic in a cell to be used for recombinant protein production. Also observed, however, is the growth and morphology of each strain. Initially, a rapid growth rate, combined with a loose, homogeneous distribution of mycelia, with neither large pellets nor aggregates formed in culture, is considered indicative of a good candidate for use in the fermentor. Based on this initial screening, strains of the following species are selected for testing in fermentors: *Thermoascus thermophilus, Mucor pusilus, Myceliophthora thermophila, Thielavia terrestris, Acremonium alabamense* (the imperfect form of *Thielavia terrestris*), *Talaromyces emersonii*, and *Sporotrichum cellulophilum*.

Figure 1:
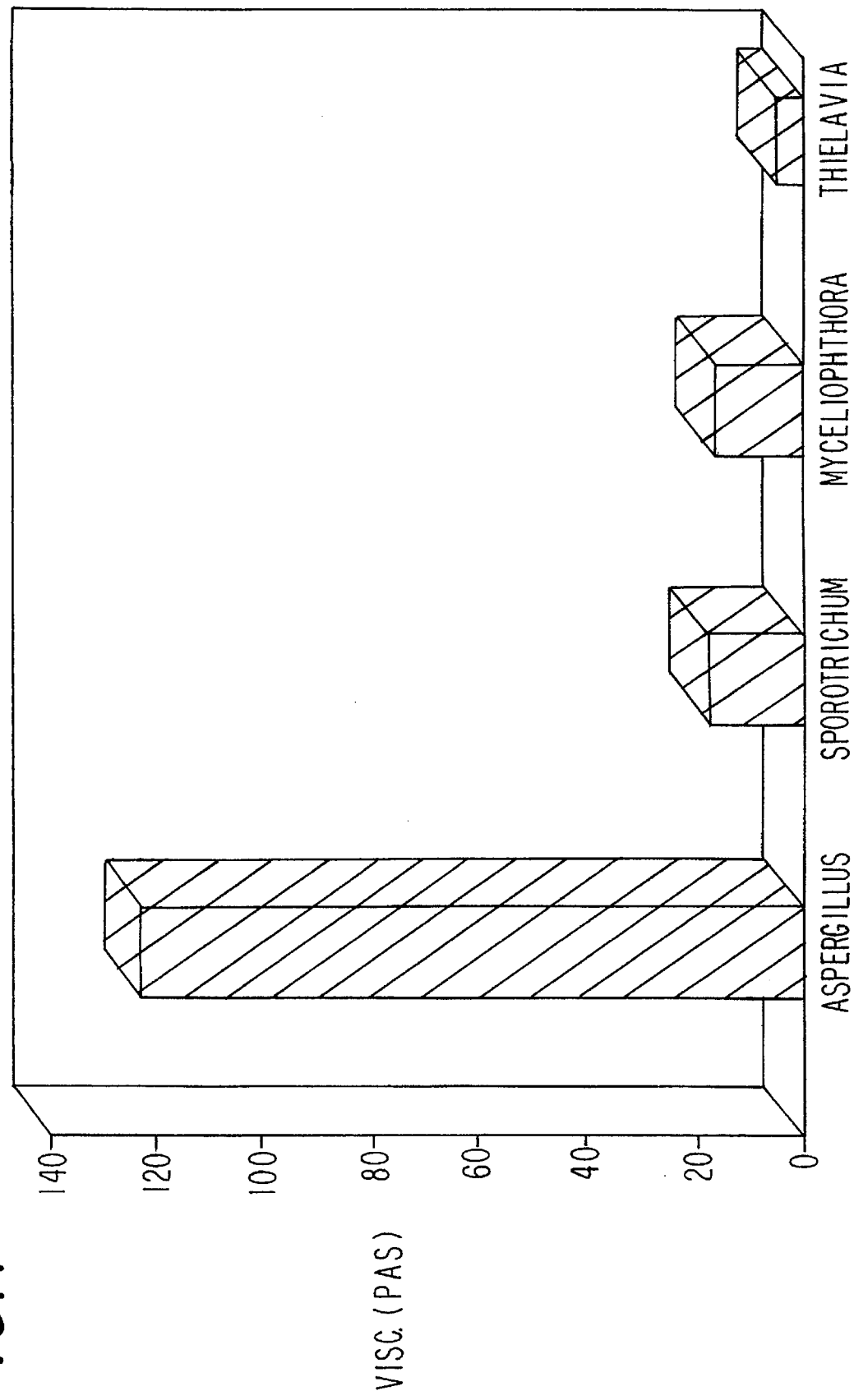
FIG. 1 illustrates the viscosity in batch fermentation, measured in pascal, and extrapolated to 30 g/l, of a number of thermophilic fungi compared with that of Aspergillus oryzae.

The candidate strains are tested in six 100 g/l glucose batch fermentation runs and analyzed for viscosity, with *Aspergillus oryzae* as the control. *Mucor pusilus* produces a large cake of mycelia, and *Talaromyces* strains produces high levels of protease, and therefore, are dropped from further studies. The data for the remaining strains, provided in Table 1, illustrates that the viscosity levels of the thermophiles tested are substantially (i.e., at least about 50%) lower than the levels observed with *Aspergillus oryzae* at equivalent biomasses. An extrapolation of these data, comparing the strains at 30 g/l of biomass, is shown in FIG. 1. Based strictly on the observations on viscosity, *Thielavia terrestris* appears to have the most favorable profile. The mycelia in this species are homogeneously dispersed, forming a loose structure of close, highly branched mycelia. *Myceliophthora* is similar to *Thielavia* but has an elongated and less branched growth form, resulting in a somewhat higher viscosity than seen with *Thielavia*. Both *Thermoascus* and *Sporotrichum* also exhibit a useful morphology and very little viscosity.

In addition to exhibiting a useful morphology, the candidate host cell must of course be transformable and capable of expressing heterologous protein. Although thermophilic fungi, e.g., *Humicola grisea* var. thermoidea, have previously been transformed (Allison et al., Curr. Genet. 21:225–229, 1992), the expression of heterologous proteins in a recombinant fungal cell has not been reported. Therefore, it was initially unclear that these thermophiles would ultimately prove useful at all in recombinant heterologous protein production. Surprisingly, however, as shown in the Examples below, the standard *Aspergillus* transformation protocols (as described in, for example, Christiansen et al., Bio/Technol. 6:1419–1422) can be used to transform a majority of the strains tested. Thus, the thermophilic fungi of the present invention provide the requisite properties for use as host cells in recombinant protein production in fermentors, both with regard to transformability and advantageous morphology.

The use of thermophilic fungi as host cells provides other advantages as well. In addition to the lower viscosity observed in culture of these fungi, the higher temperature at which they are grown is conducive to a more rapid growth rate in some species than is seen with non-thermophiles. This in turn leads to a more rapid accumulation of biomass, which results in a relatively short fermentation cycle. Also, in continuous fermentation, the combination of the higher temperatures with the lower pH which these fungi favor provides conditions in which risk of contamination is significantly reduced.

The present invention encompasses any thermophilic fungus which meets the viscosity requirements as defined above during fermentation. By "thermophilic fungus" is meant any fungus which exhibits optimum growth at a temperature of at least about 40° C., preferably between 50° C. This includes, but is not limited to, the thermophilic members of the genera Acremonium, Corynascus, Thielavia, Myceliophthora, Thermoascus, Sporotrichum, Chaetomium, Ctenomyces, Scytalidium, and Talaromyces. In a preferred embodiment, the thermophile is selected from the group consisting of strains of *Thermosascus thermophilus, Myceliophthora thermophila, Sporotrichum cellulophilum,* and *Thielavia terrestris*. It will be understood that for the aforementioned species, the invention encompasses both the perfect and imperfect states, and other taxonomic equivalents, e.g., anamorphs, regardless of the species name by which they are known. For example, the imperfect form of *Thielavia terrestris* is known as *Acremonium alabamense,* and *Myceliophthora thermophila* is *Thielavia heterothallica*. Further examples of taxonomic equivalents and other useful species can be found, for example, in Cannon, Mycopathologica 111: 75–83,1990; Moustafa et al., Persoonia 14: 173–175, 1990; Stalpers, Stud. Mycol. 24, 1984; Upadhyay et al., Mycopathologia 87: 71–80, 1984; Subramanian et al., Cryptog. Mycol. 1: 175–185, 1980; Guarro et al., Mycotaxon 23: 419–427, 1985; Awao et al., Mycotaxon 16: 436–440, 1983; von Klopotek, Arch. Microbiol. 98:365–369, 1974; and Long et al., 1994, ATCC Names of Industrial Fungi, ATCC, Rockville, Md. Those skilled in the art will readily recognize the identity of appropriate equivalents.

As the results presented in the examples show, several isolates of each species possess the morphology required to make them useful in fermentation. It is also shown that the ability to be transformed is not limited to a single thermophilic species. Thus, it is understood that the utility is not limited to a single isolate or strain, but rather is a characteristic of a group of species. Those skilled in the art will recognize that other strains or isolates of these species can also be used in expression of heterologous expression. Many strains of each species are publicly available in the collections of the American Type Culture Collection (ATCC) 12301 Parklawn Drive, Rockville Md. 20852; Agricultural Research Service Culture Collection (NRRL) 1815 North University Street, Peoria, Ill. 61604; Fungal Genetics Stock Center (FGSC), Kansas; Deutsche Sammlung yon Mikroorganismen und Zellkulturen (DSM), Mascheroder Weg 1B, D-3300 Braunschweig, Germany; Institute of Applied Microbiology (IAM), Tokyo University 1-1,1-Chome, Yayoi, Bunkyo-ku, Tokyo 113, Japan; Institute for Fermentation (IFO), 17-85 Juso-honmachi 2-chome, Yodogawaku, Osaka 532, Japan; and Centraal Bureau voor Schimmelcultures (CBS), Oosterstraat 1, 3740 AG Baarn, Netherlands, and are also available in the culture collection of Novo Nordisk Biotech, Davis, Calif.

Suitability of other thermophilic fungal hosts for use in fermentors can readily be determined by the methods described in the following examples. Briefly, candidate fungi are cultured on standard growth medium such as salts/yeast extract, soya, potato protein, or any medium supplemented with glucose or other appropriate carbon source. The fermentation is carried out at a pH of about 4–7 and at a temperature of from about 37°–50° C., preferably at about 42°–46 C. It will of course be recognized that the temperature of the control fermentation should be that which is optimum for the control strain; for *A. oryzae*, this is about 32°–36° C. It is possible to identify qualitatively those strains which will be useful for fermentation by visual inspection of mycelial morphology, in shake flasks; useful strains will show a loose, homogeneous arrangement of mycelium with many branching points. Confirmation of utility is best determined in fermentors, by evaluating actual viscosity of the culture medium at various time points in the fermentation. Viscosity determination can be made by any means known in the art, e.g., Brookfield rotational viscometry (defined or unlimited shear distance and any type of spindle configuration), kinematic viscosity tubes (flow-through tubes), falling ball viscometer or cup-type viscometer. Preferably, in the evaluation, a strain of *A. oryzae* is included as a control with which the viscosity of the candidate strain is compared. The preferred host cells exhibit about 80% or less of the viscosity level produced by an *A. oryzae* strain under identical fermentation conditions, preferably about 50% or less, and most preferably about 30% or less.

The skilled artisan will also recognize that the successful transformation of the host species described herein is not limited to the use of the vectors, promoters, and selection markers specifically exemplified. Generally speaking, those techniques which are useful in transformation of *A. oryzae*, *A. niger* and *A. nidulans* are also useful with the host cells of the present invention. For example, although the amdS selection markers are preferred, other useful selection markers include, but are not limited to, the argB (*A. nidulans* or *A. niger*), trpC (*A. niger* or *A. nidulans*), pyrG (*A. niger* or *A. nidulans*), sC(selenate resistance) or glufosinate resistance(*A. oryzae*) markers, or their equivalents from other species. The promoter may be any DNA sequence that shows strong transcriptional activity in these species, and may be derived from genes encoding both extracellular and intracellular proteins, such as amylases, xylanases, glucoamylases, proteases, lipases, cellulases and glycolytic enzymes. Such suitable promoters may be derived from genes for *A. oryzae* TAKA amylase, *Rhizomucor miehei* aspartic proteinase, *A. niger* glucoamylase, *A. niger* neutral α-amylase, *A. niger* acid stable α-amylase, and *Rhizomucor miehei* lipase. Examples of promoters from genes for glycolytic enzymes are TPI, ADH, and PGK. The promoter may also be a homologous promoter, i.e., the promoter for a gene native to the host strain being used. A useful promoter according to the present invention is the *A. oryzae* TAKA amylase promoter. The TAKA amylase is a well-known α-amylase (Toda et al., Proc.Japan Acad. 58 Ser. B.: 208–212, 1982). The promoter sequence may also be provided with linkers for the purpose of introducing specific restriction sites facilitating ligation of the promoter sequence with the gene of choice or with a selected signal peptide or preregion. Terminators and polyadenylation sequences may also be derived from the same sources as the promoters. Enhancer sequences may also be inserted into the construct.

To avoid the necessity of disrupting the cell to obtain the expressed product, and to minimize the amount of possible degradation of the expressed product within the cell, it is preferred that the product be secreted outside the cell. To this end, in a preferred embodiment, the gene of interest is linked to a preregion such as a signal or leader peptide which can direct the expressed product into the cell's secretory pathway. The preregion may be derived from genes for any secreted protein from any organism, or may be the native preregion. Among useful available sources for such a preregion are a glucoamylase or an amylase gene from an Aspergillus species, an amylase gene from a Bacillus species, a lipase or proteinase gene from *Rhizomucor miehei*, the gene for the α-factor from *Saccharomyces cerevisiae*, or the calf prochymosin gene. Most preferably the preregion is derived from the gene for *A. oryzae* TAKA amylase, *A. niger* neutral α-amylase, *A. niger* acid stable α-amylase, *B. licheniformis* α-amylase, the maltogenic amylase from Bacillus NCIB 11837, *B. stearothermophilus* α-amylase, or *B. licheniformis* subtilisin. An effective signal sequence is the *A. oryzae* TAKA amylase signal, the *Rhizomucor miehei* aspartic proteinase signal and the *Rhizomucor miehei* lipase signal. As an alternative, the preregion native to the gene being expressed may also be used.

The gene for the desired product functionally linked to promoter and terminator sequences may be incorporated in a vector containing the selection marker or may be placed on a separate vector or plasmid capable of being integrated into the genome of the host strain. The vector system may be a single vector or plasmid or two or more vectors or plasmids which together contain the total DNA to be integrated into the genome. Vectors or plasmids may be linear or closed circular molecules. According to a preferred embodiment of the present invention, the host is transformed with two vectors, one including the selection marker and the other comprising the remaining heterologous DNA to be introduced, including promoter, the gene for the desired protein and transcription terminator and polyadenylation sequences.

The present host cell species can be used to express any prokaryotic or eukaryotic heterologous peptide or protein of interest, and is preferably used to express eukaryotic peptides or proteins. The species *Thielavia terrestris* is particularly useful in that it recognized as having a safe history. Of particular interest for these species is their use in expression of heterologous proteins, especially fungal enzymes. The novel expression systems can be used to express enzymes such as catalase, laccase, phenoloxidase, oxidase, oxidoreductases, cellulase, xylanase, peroxidase, lipase, hydrolase, esterase, cutinase, protease and other proteolytic enzymes, aminopeptidase, carboxypeptidase, phytase, lyase, pectinase and other pectinolytic enzymes, amylase, glucoamylase, α-galactosidase, β-galactosidase, α-glucosidase, β-glucosidase, mannosidase, isomerase, invertase, transferase, ribonuclease, chitinase, mutanase and deoxyribonuclease. It will be understood by those skilled in the art that the term "fungal enzymes" includes not only native fungal enzymes, but also those fungal enzymes which have been modified by amino acid substitutions, deletions, additions, or other modifications which may be made to enhance activity, thermostability, pH tolerance and the like.

The present host cells may also be used in recombinant production of proteins which are native to the host cells. Examples of such use include, but are not limited to, placing a thermophile's native protein under the control of a different promoter to enhance expression of the protein, to expedite export of a native protein of interest outside the cell by use of a signal sequence, or to increase copy number of a protein which is normally produced by the subject host cells. Thus, the present invention also encompasses, within the scope of the term "heterologous protein", such recombinant production of homologous proteins, to the extent that such expression involves the use of genetic elements not native to the host cell, or use of native elements which have been manipulated to function in a manner not normally seen in the host cell.

As noted above, *Thielavia terrestris* is, because of its excellent morphology, among the preferred species for use in recombinant protein production. However, this species, in submerged culture, is also subject to loss of biomass, by virtue of sporulation, under conditions of limitation of growth (either glucose or oxygen). Specifically, the large amounts of mycelia produced during early stages of fermentation may rapidly disappear and large quantities of spores appear. Since the mycelia are the source of production of the recombinant proteins, avoiding sporulation in culture is desirable. To this end, a non-sporulating mutant of Thielavia is isolated. Spores are exposed to ultraviolet light and cultivated for five days. The mycelia are then spread on plates and incubated for 24 hours. The eight largest colonies are chosen, on the assumption that mycelial fragments grow faster than spores which first have to germinate, and tested in shake flasks. Two out of the eight colonies show no sporulation in submerged culture, showing this to be a viable approach in the production of non-sporulating strains if the need arises.

The present invention will be further illustrated by the following non-limiting examples.

I. Shake Flask Evaluation of thermophiles

ASPO4 medium having the following composition, with variable carbon source, is used in shake flasks:

| | |
|---|---|
| Yeast extract | 2 g/l |
| $MgSO_4.7H_2O$ | 1 g/l |
| $CaCl_2$ | 1 g/l |
| $KH_2PO_4$ | 5 g/l |
| Citric acid | 2 g/l |
| Trace metals* | 0.5 ml/l |
| Urea | 1 g/l |
| $(NH_4)_2SO_4$ | 2 g/l |

*contains 14.3 g/l $ZnSO_4.7H_2O$, $CuSO_4.5H_2O$, 0.5 g/l $NiCl_2.6H_2O$, 13.8 g/l $FeSO_4.7H_2O$, 8.5 g/l $MnSO_4.H_2O$, and 3 g/l citric acid
Propylene shake flashs (100 or 500 ml) without baffles are used, shaken at 200 rpm at a temperature of 42–44° C., pH 4.5.

A number of thermophilic strains are screened in shake flasks for the following characteristics: (1) vigor of growth; (2) protease production; (3) secreted proteins; and (4) mycelial morphology. To determine protease activity, supernatant from the culture broth of each is spun at 2500 rpm for 5 minutes, and used in the casein clearing plate assay, which determines the levels of proteases produced by various fungal species being evaluated as potential candidates for recombinant protein expression.

The casein plate clearing assay is conducted as follows. The plate medium is composed of 20 g/l skim milk, 20 g/l agarose, and 0.2M citrate-phosphate buffer for tests run at pH 5 and pH 7, and glycine NaOH buffer for tests run at pH 9. Milk powder is mixed with 100 ml of buffer and kept at 60° C. Agarose is mixed with 400 ml of buffer and autoclaved 5 minutes. After slight cooling, the warm milk mixture is added, and the mixture inverted gently 2–3 times to mix. The medium is poured into 150 mm plates using 50–70 ml per plate and stored at 5° C. until use.

Just prior to use, twelve holes per plate are made in the agar. 25 µl of supernatant from fermentation of each strain is added to one plate of each pH and incubated overnight at 37° C. To pH 9 plates, 0.5M glacial acetic acid is added to precipitate casein and allow visualization of any clear zones. Each plate is then evaluated on clear zone size (i.e., from no zone to >2 cm in diameter) and zone type (i.e., clear, opaque or both types).

The supernatants of each culture are also used to evaluate the strains' extracellular protein production. Novex 8–16% SDS polyacrylamide gradient gels, prepared according to manufacturer's instructions, are used to assess the protein profile. A 40 µl (48 hour) sample of culture supernatant is mixed with 10 µl of 5X dissociation buffer (dissociation buffer=4 ml 1M Tris-HCl, pH 6.8, 1 g SDS, 617 mg dithiothreitol, and sterile distilled water to 10 ml), and glycerol/bromophenol blue (10–20 mg added to about 10 ml of 80–90% glycerol, and placed in boiling water for 1–2 hours to dissolve), boiled for 5 minutes, cooled, loaded and run at 120 V until the bromphenol blue tracking dye reaches the bottom of the gel. The gels are stained with Coomasie brilliant blue. Those isolates showing large numbers of bands are considered less suitable as potential new hosts.

Growth is evaluated qualitatively, on a + to +++ scale. Morphology is ranked as follows: 1-long close interacting hyphae with very little branching; 2-many conidia spores, with very pronounced branching; 3-thin, long, straight hyphae with some branching; 4-thick, short, irregular hyphae with lots of branching; 5-loose mycelium with very pronounced branching; 6-loose branched mycelium with very homogeneous mycelium distribution; 7-long close interacting hyphae with some branching. Morphologies 5 and 6 are considered the most desirable.

Five experiments in shake flasks are conducted, in which the identity and amount of carbon source are varied, as follow: (1) maltodextrin 10 g/l; (2) glucose 10 g/l; (3) maltodextrin 20 g/l; (4) 10 g/l Avicell+1 g/l glucose [for induction of cellulases]; (5) 30 g/l maltodextrin+10 g/l glucose. The isolates of the species tested, in one or more of the experiments, are: *Talaromyces emersonii, T. byssochlamydoides, Thielavia terrestris, Thermoascus thermophilus, T. aurantiacus, Malbranchea sulfurea, Melanocarpus albomyces, Sporotrichum cellulophilum, Acremonium alabamense, Humicola grisea* var. *thermoidea, Mucor pusilus, Myceliophthora thermophila,* and *Scytalidium thermophilum*. Several of these strains exhibit useful morphology and vigorous growth under one or more of the experimental conditions defined above. Under the conditions tested, none of the strains tested secrete high (>1 g/l) levels of any protein, and are considered to have a clean protein background. Several of the strains show high protease activity (e.g., *Talaromyces emersonii, Talaromyces byssochlamydoides*) and some grow very poorly under the tested growth conditions (e.g., *Malbranchea sulfurea*). None of these are tested further.

In the course of this evaluation, the extent of sporulation in submerged culture and on plates is determined. The ability to sporulate on plates is virtually essential for in a useful host cell. Of the species of interest, neither *Thielavia terrestris* nor *Myceliophthora thermophila* show any spores on normal fungal agar plates. Methods for sporulation are then developed for these two species. For Myceliophthora, mycelium is first grown on potato dextrose agar(PDA; Difco) plates at 37° C. for 48 hours, then grown overnight at 50° C., then grown an additional 24–48 hours at 37° C. Temperature stress apparently triggers sporulation in this species.

With Thielavia, sporulation on plates can be induced by first incubating mycelium on PDA plates for three days in the normal atmosphere of a 37° C. incubation room. The culture is then placed in a 1 liter Pyrex® beaker that is flushed with $N_2$ gas, sealed with plastic wrap, and returned to the 37° C. room for 48 hours. The plate is removed from the beaker to the normal atmosphere of the room and left to incubate for one week. The plate develops a ring of off-white spores between the pre- and post-$N_2$ treated growth. This sporulation is apparently triggered by oxygen stress.

Oxygen limitation, as well as glucose limitation, also triggers sporulation of Thielavia in submerged culture. In fact, such sporulation occurs spontaneously after 3–4 days in ASPO4 medium with 20 g/l glucose. However, under fermentation conditions, this sporulation is undesirable, as the mycelial biomass rapidly disappears and is replaced by spores, thereby reducing productivity. To overcome this problem, a nonsporulating strain is created from *Thielavia terrestris* E373. A shake flask with $10^6$ UV-exposed(30 seconds exposure leading to 40% kill) spores/ml of medium(ASPO4 with 2 g/l glucose) is cultivated for 5 days at 42° C. Mycelium for this culture is diluted in 0.1% Tween solution spread on PDA plates, and incubated 24 hours at 42° C. The eight largest colonies are picked, based on the assumption that mycelium fragments will grow faster than spores, which must first germinate. The selected colonies are transferred to shake flasks; two out of the eight selected do not sporulate at all in these submerged cultures, while the other six show some degree of sporulation.

Chosen for initial study in tank fermentation are *Thielavia terrestris* (strains E373 and ATCC 20627), *Myceliophthora thermophila* (strain A421), *Sporotrichum cellulophilum* (strain ATCC 20493), and *Thermoascus thermophilus* (strains 2050 and CBS 759.71), *Mucor pusilus* (strain A209), *Acremonium alabamense* (A2082), *Talaromyces emersonii* (strain A577). Strains designated "A" are available in the culture collection of Novo Nordisk A/S, Bagsværd, Denmark; strains designated "E" are available in the culture collection of Novo Nordisk Entotech, Davis, Calif.

II. Fermentor Evaluation

The medium used in tank fermentation is as follow:

|  | Batch |
|---|---|
| $MgSO_4.7H_2O$ | 2 g/l |
| $KH_2PO_4$ | 5 g/l |
| Citric acid.$1H_2O$ | 4 g/l |
| Yeast extract | 10 g/l |
| $NH_4$sulfate | 10 g/l |
| $CaCl_2$ | 2 g/l |
| AMG trace metals* | 0.5 ml/l |
| Pluronic | 1 ml/l |

*contains $ZnSO_4.7H_2O$ 14.3 g/l; $CuSO_45H_2O$ 2.5 g/l; $NiCl_2.6H_2O$ 0.5 g/l; $FeSO_4.7H_2O$ 13.8 g/l; $MnSO_4.H_2O$ 8.5 g/l; citric acid 3.0 g/l
Tap water is used, and pH is adjusted to 6 before autoclaving.
Carbon source: 50% glucose added to 100 g/l based on initial volume (2 l)

Fermentation is conducted at 42°–46° C., at pH 5.0, +/−0.1, adjusted with $H_3PO_4$ or NaOH. Applicon fermentors with increased impeller size are used. The concentration of dissolved oxygen(DOT) is kept >20% of saturation concentration with an aeration rate of 1 volume per volume per minute and agitation speed between 800–1400 rpm.

Biomass concentration is estimated by dry cell weight. Twenty mls of cultures are filtered through preweighed 20 μm membranes. Filter cakes are washed twice with $H_2O$, dried 48 hours at 96° C. and weighed. Viscosity is determined with a Bohlin Reologi, Inc. "Visco 88" which is equipped with the "C14" cup-and cylinder system. The system switch is set to "1" and the speed is set to "8". This turns the cylinder within the cup at 1000 rpm and delives a shear rate of 1222/s. Whole culture samples are removed from fermentors and measured within two minutes on room temperature equipment. Approximately 10 mLs of sample is put into the cup which in turn is fixed onto the visco 88 with the cylinder fully submerged. The initial viscosity reading, produced within seconds of the start of cylinder rotation, is recorded.

Six fermentation runs of *T. terrestris* E373 and ATCC 20627, *M. thermophila* 421, *S. cellulophilum* ATCC 20493, *T. thermophilus* A2050 and *A. oryzae* A1560 (control) are analyzed for viscosity. All runs are 100 g/l glucose batch fermentations at pH 5 and 1100 rpm. The thermophilic strains are grown at 42° C. and *A. oryzae* is grown at 37° C. The data are presented in Table 1, showing viscosity values in pascal; the lower the pascal value, the less viscous the culture. The measured viscosity data are for fresh samples measured during the first seconds of testing in the rheometer. The extrapolated viscosity data, comparing the strains at 30 g/l biomass are shown in FIG. 1.

TABLE 1

Comparative viscosities of thermophiles

| STRAIN | TIME (h) | BIOMASS (g/l) | VISCOSITY (pascal) |
|---|---|---|---|
| Aspergillus | 24 | 34.1 | 0.473 |
| oryzae, A1560 | 43.5 | 36.9 | 0.399 |
|  | 51.5 | 27.6 | 0.217 |
| Thielavia | 24 | 29.2 | 0.028 |
| terrestris, E373 | 43.5 | 33.5 | 0.013 |
| Myceliphthora | 24 | 20.9 | 0.045 |
| thermophila, A421 | 43.5 | 30.3 | 0.094 |
|  | 51.5 | 27.8 | 0.035 |
| Sporotrichum | 17.5 | 22.2 | 0.065 |
| cellulophilum, | 24 | 30.0 | 0.096 |
| ATCC 20493 | 40 | 46.8 | 0.144 |
|  | 47 | 52.9 | 0.178 |
| Thielavia | 24 | 6.1 | 0.018 |
| terrestris, ATCC 20627 | 40 | 51.1 | 0.016 |
| Thermoascus | 40 | 17.4 | 0.025 |
| thermophilus, | 47 | 22.4 | 0.037 |
| A2050 | 71.5 | 31.6 | 0.042 |
|  | 112 | 36.6 | 0.053 |

As the data show, by far the most viscous strain is the control *A. oryzae* strain. The least viscous strains are the two Thielavia strains. These strains are observed to be easily mixed and aerated in the fermentors and show a very homogeneously dispersed mycelium, which forms a loose structure of closely associated, highly branched mycelia that continuously break up during growth. Neither big pellets nor aggregates are formed.

The Myceliophthora strain is very similar to Thielavia, but gives an elongated and less branched growth form, resulting in somewhat greater viscosity. Measurements on Acremonium are not obtained, but visual observation indicates that it shows a morphology and viscosity similar to Thielavia. Thermoascus also shows good morphology, similar to Thielavia. Sporotrichum is also good morphologically, but produces large amounts of a green pigment and starts to lyse under these fermentation conditions. *Mucor pusilus* produces a less than optimum morphology, with one large cake of mycelia, and is not analyzed further. Talaromyces also is not taken further because it produces higher amounts of protease activity than the other strains. Table 2 illustrates data for growth rates, measured at biomass concentrations of 2–15 g/l, and for protease production for the strains tested in the fermentor. Growth rate is estimated from the growth curve, where an almost linear biomass increase is seen from 2–15 g/l dry biomass concentration(biomass is determined by filtration, drying and weighing remaining mycelium on the filter.

TABLE 2

Growth rate and protease formation in glucose batch fermentations at pH5 and 42° C.

| STRAIN | GROWTH RATE RELATIVE TO A. ORYZAE | PROTEASE PRODUCTION |
| --- | --- | --- |
| Thermoascus thermophilus | 1× | low protease |
| Mucor pusilus | 2.5× | very high protease(all) |
| Myceliophthora thermophila | 1× | very high alkaline protease |
| Thielavia terrestris | 3× | high acid protese |
| Acremonium alabamense | 3× | high acid protese |
| Talaromyces emersonii | 1× | very high protease (mainly acidic) |
| Sporotrichum cellulophilum | 2× | some protease (mainly acidic) |

Figure 3:
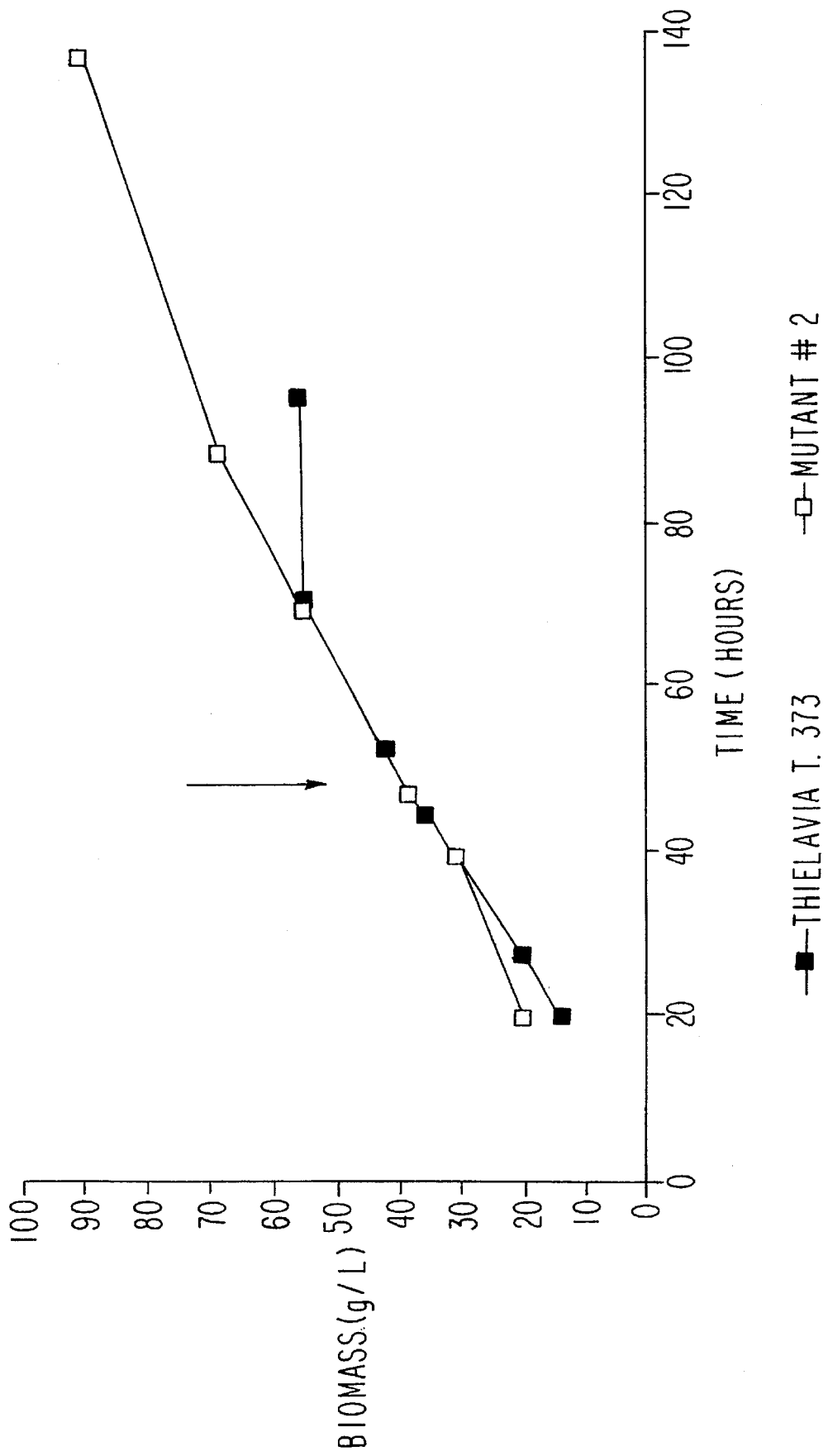
FIG. 3 illustrates the increase in biomass over time for Thielavia terrestris 373, and a nonsporulating mutant of the same strain. The arrow indicates the point in time at which the 373 strain begins to sporulate.

Another method for evaluating fungal morphology and to determine how suitable it is for submerged tank fermentation is to attempt to obtain very high biomass concentration. With unicellular organisms, such as E. coli and S. cerevisiae, it is possible to reach biomass concentration close to 100 g/l, but with fungi it is very difficult to reach a level greater than 75 g/l. The upper limit (caused by high viscosity and lack of oxygen transfer) for A. oryzae and A. niger is about 50–60 g/l. Thielavia terrestris E373 and the nonsporulating mutant described above are tested in submerged culture. Fermentation is at pH 5, 42° C. and in medium that is double strength compared to earlier described batch medium (200 g/l glucose). The nonsporulating mutant achieves a biomass of about 90 g/l after 140 hours (FIG. 3). This is an unusually high biomass concentration in a fungal fermentation, and clearly demonstrates the superiority of the strains having this type of morphology.

II. Expression of heterologous genes in thermophiles

A. Selectable marker vectors. The vector pJaL77 is used in transformation of host cells with the hygromycin B resistance selectable marker. This marker is based on the E. coli hygromycin B phosphotransferase gene, which is under the control of the TAKA promoter. Briefly, the vector is constructed as follows. The gene conferring resistance to hygromycin B is purchased from Boehringer Mannheim as plasmid pHph-1. This gene is equipped with an ATG codon as well as with suitable restriction sites at the amino and carboxy termini by PCR, using the primers: 5'-GCT CAG AAGCTT CCATCC TAC ACC TCA GCA ATG TCG CCT GAA CTC ACC GCG ACG TCT-3' (N-terminal) (SEQ ID NO:1) and 3'-CGT CCG AGG GCA AAG GAA TAG CTCCAG AGATCT CAT GCT-5'(C-terminal) (SEQ ID NO:2). The PCR fragment is cut with the restriction enzymes BamHI and XhoI and cloned into the corresponding sites in the Aspergillus expression vector pToC68 (as described in WO 91/17243) to produce pJaL77.

The plasmid pToC90 containing the amdS marker is constructed by cloning a 2.7 kb XbaI fragment from p3SR2 (Hynes et al. Mol. Cell. Biol. 3(8): 1430–1439, 1983) into an XbaI cut and dephosphorylated pUC19 plasmid.

B. Expression vector. The vector pHD414 is a derivative of the plasmid p775(EP 238 023). In contrast to this plasmid, pHD414 has a string of unique restriction sites between the TAKA promoter and the AMG terminator. The plasmid is constructed by removal of an approximately 200 bp long fragment (containing undesirable RE sites) at the 3' end of the terminator, and subsequent removal of an approximately 250 bp long fragment at the 5' end of the promoter, also containing undesirable sites. The 200 bp region is removed by cleavage with NarI (positioned in the pUC vector) and XbaI (just 3' to the terminator), subsequent filling in the generated ends with Klenow DNA polymerase+dNTP, purification of the vector fragment on a gel and religation of the vector fragment. This plasmid is called pHD413. pHD413 is cut with StuI (positioned in the 5' end of the promoter) and PvuII (in the pUC vector), fractionated on gel and religated, resulting in pHD414. A strain of E. coli containing the approximately 1,100 bp xylanase HindII/XbaI cDNA fragment in pYES is deposited in DSM as DSM 6995. The xylanase cDNA fragment is isolated from one of the clones by cleavage with HindIII/XbaI. The fragment is purified by agarose gel electrophoresis, electroeluted, and made ready for ligation reactions. The cDNA fragment is ligated into pHD414 to produce pAXX40-1-1, which is deposited as NRRL B-21164. The xylanase gene is deposited as DSM (Deutsche Sammlung Von Mikrooroganismen und Zellkulturen GmbH) 6995.

III. Transformation of Thermoohilic Hosts

The following general procedures are used in transformation of all the strains tested, with exceptions noted expressly:

100 ml of MY51 medium (maltodextrin, 30 g/l; $MgSO_4 \cdot 7H_2O$, 2 g/l; $K_2PO_4$, 10 g/l, $K_2SO_4$, 2 g/l; citric acid, 2 g/l; yeast extract, 10 g/l; AMG trace metals, 0.5 ml; urea 1 g/l; $(NH_2)SO_4$, 2 g/l, pH 6.0) is inoculated with mycelial plugs (2 cm diameter) of the strain to be transformed and incubated with shaking at 42° C. for 14 hours. The mycelium is harvested by filtration through miracloth and washed with 200 ml of 0.6M $MgSO_4$. The mycelium is suspended in 15 ml of 1.2M $MgSO_4$, 10 mM$NaH_2PO_4$, pH=5.8. The suspension is cooled on ice and 1 ml of buffer containing 120 mg of Novozyme® 234 is added. After 5 minutes, 1 ml of 12 mg/ml BSA (Sigma type H25) is added and incubation with gentle agitation continued for 1–3 hours, depending on the strain, at 30° C. until a large number of protoplasts are visible in a sample inspected under the microscope. For Acremonium and Thielavia, protoplasting efficiency is relatively low, and these strains require longer incubation periods (2–3 hours) until sufficient protoplasts are obtained for transformation.

The suspension is filtered through miracloth, the filtrate is transferred to a sterile tube and overlaid with 5 ml of 0.6M sorbitol, 100 mMTris-HCl, pH=7.0. Centrifugation is performed for 15 minutes at 2500 rpm and the protoplasts are collected from the top of the $MgSO_4$ cushion. Two volumes of STC (1.2M sorbitol, 10 mM Tris-HCl pH=7.5, 10 mM $CaCl_2$) are added to the protoplast suspension and the mixture is centrifuged for five minutes at 2500 rpm. The protoplast pellet is resuspended in 3 ml of STC and repelleted. This is repeated, and then the protoplasts are resuspended in 0.2–1 ml of STC.

100 µl of protoplast suspension is mixed with 5–25 µg of the appropriate DNA in 10 µl of STC. Each strain is cotransformed with pAXX40-1-1 and a plasmid containing a selectable marker. Plasmids pToC90 contains the A. nidulans amdS gene, and is used for transformation and selection for growth on acetamide as the sole nitrogen source. Plasmids pJaL77 is used for transformation and selection of resistance to hygromycin B (150 µg/ml).

The mixtures are left at room temperature for 25 minutes. 0.2 ml of 60% PEG 4000 (BDH 29576), 10 mM $CaCl_2$ and 10 mMTris-HCl pH=7.5 is added and carefully mixed twice and finally 0.85 ml of the same solution is added and carefully mixed. The mixture is left at room temperature for 25 minutes, spun at 2500 X g for 15 minutes and the pellet resuspended in 2 ml of 1.2M sorbitol. After one more sedimentation the protoplasts are spread on the appropriate plates. protoplasts are spread on minimal plates (Cove, Biochem. Biophys. Acta 113: 51–56, 1966) containing 1.0M sucrose, pH=7.0, 10 mM acetamide as nitrogen source (when amdS is the selection marker) and 20 mM CsCl to inhibit background growth. The medium differs when hygB is the selection marker in the use of 10 mM sodium nitrate as nitrogen source, and the presence of 150 μg/ml hygromycin B. The selection plates are incubated at 42° C. for 5 days. All the transformants which grow on COVE selection medium are transferred to COVE II(COVE medium without calcium chloride and with a sucrose concentration of 30 g/l) plates containing AZCL-xylan (0.2%) and the respective selection agent. Cotransformants are identified by the rapid formation of a blue halo in and around the fungal colony. The results of transformation experiments and the number of cotransformants identified are given in Table 3.

TABLE 3

Results of transformation of thermophiles

| STRAIN | SELECTION | NUMBER OF TRANS-FORMANTS | NUMBER OF CO-TRANS-FORMANTS |
| --- | --- | --- | --- |
| Myceliophthora | amdS | 42 | 18 |
|  | HygB | 0 | 0 |
| Sporotrichum | amdS | 35 | 15 |
|  | HygB | 0 | 0 |
| Thielavia | amdS | 18 | 4 |
|  | HygB | 0 | 0 |
| Acremonium | amdS | 23 | 10 |
|  | HygB | 0 | 0 |

Hygromycin selection is not successful in any of the thermophilic fungi investigated presumably because the promoter is not efficient in these strains. However, with amdS selection, transformants are obtained in all strains except Thermoascus. Co-transformation frequency is between 20–40%.

D. Evaluation of xylanase expression in transformants

All the co-transformants identified by xylanase-plate assays are subjected to shake flask evaluation for xylanase productivity. M401 medium of the following composition (g/l) is used: maltodextrin, 50.0; MgSO$_4$.7H$_2$O, 2.0; KH$_2$PO$_4$, 2.0; citric acid, 4.0; yeast extract, 8.0; AMG trace metal solution, 0.5 ml; ammonium sulfate, 2.0; urea, 1.0. The cultures are incubated at 42° C. and xylanase activity is measured every day starting from 24 hours. Xylanase activity in culture broths is determined using 0.2% AZCL-xylan (Megazyme Co. Australia) suspended in a citrate phosphate buffer, pH 6.5. The culture fluid is diluted, usually 100-fold, and 10 μl of diluted culture fluid is mixed with 1 ml of 0.2% AZCL-xylan substrate. The mixture is incubated at 42° C. for 30 minutes. The reaction mixture is mixed well every 5 minutes. At the end of incubation, the undigested substrate is precipitated by centrifugation at 10,000 rpm for 5 minutes. The blue dye released from this substrate is quantified by absorbance at 595 nm and the amount of enzyme activity in the culture broths is calculated from a standard made with an enzyme preparation with known activity. An endoxylanase unit (EXU) is determined relative to an enzyme standard prepared under identical conditions. Untransformed strains are also grown under identical conditions and compared with the transformants.

Figure 2:
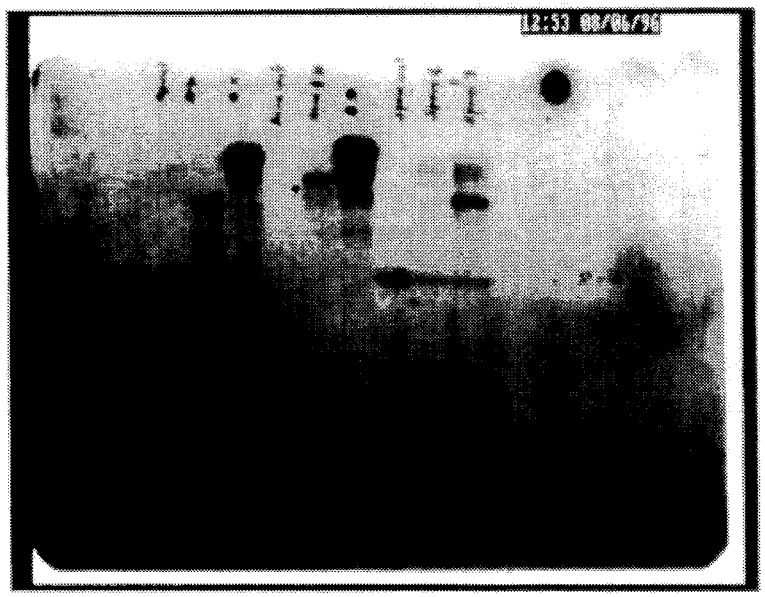
FIG. 2 shows the southern hybridization analysis of total DNA isolated from untransformed and xylanase transformants of thermophilic strains. A 1.2 kb HindIII-XhoI fragment of Humicola insolens xylanase cDNA is used as the probe. Lane 1: Myceliophthora thermophila untransformed; Lane 2: Myceliophthora thermophila transformant #5; Lane 3: Myceliophthora thermophila transformant #11; Lane 4: Acremonium alabamense untransformed; Lane 5: Acremonium alabamense transformant #5; Lane 6: Acremonium alabamense transformant #8; Lane 7: Sporotrichum cellulophilum untransformed; Lane 8: Sporotrichum cellulophilum transformant #6; Lane 9: Sporotrichum cellulophilum transformant #7.

The data presented in FIG. 2 (based on the peak of activity) indicate that all untransformed strains produce xylanase activity at very low levels, while some of the transformants produce up to 5–10 fold greater activity than the untransformed strains. SDS-PAGE analysis of the spent culture medium reveals the presence of a 22 kD *Humicola xylanase* protein band only in the transformants, although at very low levels. This illustrates the potential for expression of heterologous genes in thermophilic fungi. The order of productivity of xylanase is in the order of Myceliophthora-Sporotrichum-Acremonium-Thielavia.

E. Confirmation of Transformation and Integration of Expression Vectors

To unequivocally demonstrate the transformation and integration of expression vectors, southern hybridization analyses are performed using total DNA isolated from untransformed and selected transformants from each strain. Two best transformants from each strain are selected for southern hybridization analyses. Total genomic DNA isolated from these strains is digested with EcoRI, DNA fragments are separated through 1% agarose gel and blotted. Since Thielavia and Acremonium represent the perfect and imperfect stages of the same strain, only DNA from Acremonium is used for the hybridization experiments. First, the blot is probed with the *Aspergillus nidulans* amdS gene, the selection marker used for transformation. The results show the presence of amdS gene only in the transformants but not in the untransformed negative controls. Reprobing of the same blot, after stripping off the amdS probe, with a 1.2 kb HindIII and XhoI fragment of *Humicola insolens* xylanase cDNA, show the following: Only the transformants of Acremonium but not the untransformed strain shows the presence of *H. insolens* cDNA hybridizing bands. The untransformed as well of transformants of Myceliophthora and Sporotrichum show the presence of an about 2 kb band hybridizing to the probe (possibly indicating the presence of DNA sequences in these strains sharing homology to the *H. insolens* xylanase gene), while the transformants show additional high molecular weight bands hybridizing to this probe.

What we claim is:

1. A recombinant Myceliophthora host strain which produces, in tank fermentation, about 80% or less of the viscosity produced by *Aspergillus oryzae* cultured under identical conditions.

2. The strain of claim 1 which produces, in tank fermentation, about 50% or less of the viscosity produced by *Aspergillus oryzae* cultured under identical conditions.

3. The strain of claim 1 which produces, in tank fermentation, about 30% or less of the viscosity produced by *Aspergillus oryzae* cultured under identical conditions.

4. The cell of claim 1 which is obtained from a thermophilic fungus.

5. The strain of claim 1 which is obtained from *Myceliophthora thermophilum*.

* * * * *